US006444681B1

(12) United States Patent
Flavahan et al.

(10) Patent No.: US 6,444,681 B1
(45) Date of Patent: Sep. 3, 2002

(54) METHODS AND COMPOSITIONS FOR TREATING RAYNAUD'S PHENOMENON AND SCLERODERMA

(75) Inventors: Nicholas Flavahan; Sheila Flavahan; Maqsood Chotani, all of Columbus; Srabani Mitra, Worthington; Baogen Su, Columbus, all of OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 09/591,254

(22) Filed: Jun. 9, 2000

(51) Int. Cl.$^7$ ............................................. A01N 43/54
(52) U.S. Cl. ........................................ 514/257; 514/259
(58) Field of Search .................................. 514/257, 259

(56) References Cited

U.S. PATENT DOCUMENTS

| 5,965,595 A | 10/1999 | Maurer et al. |
| 5,994,384 A | 11/1999 | Akerman et al. |

OTHER PUBLICATIONS

"Increased Smooth Muscle α2–Adrenergic Activity May Contribute to Vasculopathy of Scleroderma" by FLavahan, et al., *Circulation*, Oct. 21, 1997, vol. 96, No. 8, p. 1249, Abstract No. 1373.

"Silent $\alpha_{2c}$–adrenergic receptors enable cold–induced vasoconstriction in cutaneous arteries" by Chotani, et al., *Am J Physiol Heart Circ Physiol*, 278:H1075–H1083, 2000.

"Silent $\alpha_{2c}$–Adrenergic Receptors Enable Cold–Induced Vasoconstriction in Cutaneous Arteries: A Mechanism for Raynaud's Phenomenon?" by Chotani, et al., *Circulation*, vol. 100, No. 18, Nov. 2, 1999, Abstract No. 2922.

"Blockade of Vasospasitc Attacks by $\alpha_2$–Adrenergic but Not $\alpha_1$–Adrenergic Antagonists in Idiopathic Raynaud's Disease" by Freedman, et al., *Circulation*, 1995; 92:1448–1451.

α–Adrenoceptors and cold–induced vasoconstriction in human finger skin by Ekenvall, et al., *Am. J. Physiol. 255 (Heart Circ. Physiol. 24)*: pp. H1000–H1003, 1988.

"Cooling and $\alpha_1$–and $\alpha_2$–adrenergic responses in cutaneous veins: role of receptor reserve" by Flavhan, et al. *Am. J. Physiol. 249 (Heart Circ. Physiol. 18)*: pp. H950–H955, 1985.

*Primary Examiner*—Zohreh Fay
(74) *Attorney, Agent, or Firm*—Calfee, Halter & Griswold LLP

(57) ABSTRACT

A method for treating conditions or diseases associated with deleterious vasoconstriction of the small arteries and arterioles of one or more organs or parts of a patient's body. In one embodiment, the method comprises administering a therapeutically effective amount of an antagonist to the $\alpha_{2C}$-adrenergic receptor ($\alpha_{2C}$-AR) to a patient with Raynaud's Phenomenon. Such method is used to ameliorate the cold-induced or stress-induced vasoreactive response that is associated with Raynaud's Phenomenon. The $\alpha_{2C}$-AR antagonist is administered to the subject either prior to or after exposure of the patient to the cold or to stressIn another embodiment, the method is used to reduce the extent of deleterious vasoconstriction that occurs in the small arteries, arterioles, and microcirculation of the lungs, heart, kidneys, skin, or gastrointestinal tract of a patient, particularly a scleroderma patient. The method comprises administering a therapeutically effective amount of an $\alpha_{2C}$-AR antagonist to a patient who is in need of the same. Such treatment serves to maintain or restore, at least in part, blood flow through the small arteries, arterioles, and microcirculation of the lungs, heart, kidneys, skin, and/or gastrointestinal tract in a such patient. The present invention also relates to a pharmaceutical compositions comprising an $\alpha_{2C}$-AR antagonist and a pharmaceutically acceptable carrier.

18 Claims, 10 Drawing Sheets

MK 912, a benzofuroquinolizine,
1',3'-dimethylspiro(1,3,4,5',6,6',7,12b-octahydro-2H-benzo[b]furo[2,3-a]quinolizine)-2,4'-pyrimidin-2'-one

CONTROLS

SSc

METHODS AND COMPOSITIONS FOR TREATING RAYNAUD'S PHENOMENON AND SCLERODERMA

This work was supported, at least in part, by a grant from the National Institutes of Arthritis and Musculo-Skeletal and Skin Diseases Grant No: AR-46126. The United States Government has certain rights in this invention.

BACKGROUND

Raynaud's Phenomenon is one example of a disease that involves deleterious vasoconstriction of the small arteries and/or arterioles of one or more organs of a subject's body. Raynaud's Phenomenon is an abnormal vasoreactive response to cold or emotional stress of the small arteries and arterioles in the subject's digits. Individuals who suffer from Raynaud's Phenomenon experience episodic, sharp, demarcated, cutaneous pallor and cyanosis of their digits. These symptoms result from spasm or closure of the digital arteries. The condition is painful and debilitating. Under severe conditions, it can even lead to digital ulcers or amputation of the affected digit.

Another, more problematic disease that is associated with a deleterious vasoconstriction of the small arteries and arterioles in one or more organs of a subject's body is Scleroderma. Scleroderma is a devastating disease of unknown etiology or origin that is associated with severe morbidity and mortality. Vascular dysfunction is an important early defect in Scleroderma (SSc). Raynaud's phenomenon is one of the earliest manifestations of SSc, occurring in approximately 95% of patients. In addition to the digital arteries, reversible vasospasm also occurs in the terminal arterial supply of the kidney, heart, lung, and gastrointestinal tract of patients with scleroderma. Such vasospastic activity causes ischemia, reperfusion injury and increased oxidant stress of the affected organs and is thought to thereby contribute to endothelial injury and the vascular and extravascular lesions that subsequently occur in this disease. The vascular lesions are found in the small arteries, arterioles (50–500$\mu$ in diameter) and the microcirculation of the affected organ and are characterized by concentric intimal thickening and adventitial fibrosis of the small arteries and arterioles. The loss of function and structure of the affected blood vessels leads to ischemia of the organ supplied by these vessels, organ failure, and death.

At present there is no cure and no effective therapy for the diseases that involve deleterious vasoconstriction of the small arteries and arterioles, including scleroderma. In addition, there is no therapy that is specifically targeted to Raynaud's phenomenon. Current therapy for this condition is limited to broad spectrum vasodilator therapy which affects every blood vessel of the treated individual and, thus, causes significant side effects, such as dizziness, nausea, and severe headaches, vasodilator therapy could also exacerbate the problem by directing blood away from the affected organ.

Accordingly, it is desirable to have new methods and pharmaceutical compositions which can be used to treat diseases that involve deleterious vasonstriction of the small arteries and arterioles, including Raynaud's Phenomenon and scleroderma. Methods and pharmaceutical composition which do not cause systemic vasodilation are especially desirable.

SUMMARY OF THE INVENTION

The present invention provides methods for treating diseases associated with deleterious vasoconstriction of the small arteries and arterioles of one or more organs or parts of a patient's body. In one embodiment, the method comprises administering a therapeutically effective amount of an antagonist to the $\alpha_{2C}$-adrenergic receptor ($\alpha_{2C}$-AR) to a patient with Raynaud's Phenomenon. Such method is used to ameliorate the cold-induced or stress-induced vasoreactive response that is associated with Raynaud's Phenomenon. The $\alpha_{2C}$-AR antagonist is administered to the subject either prior to or after exposure of the patient to the cold or to stress. Preferably, the antagonist is administered orally or in a topical composition. To prevent or reduce the extent of the vasoconstriction that occurs when such patient is exposed to stress or cold, the $\alpha_{2C}$-AR antagonist is administered to the patient prior to such exposure. Such treatment serves to maintain, at least in part, blood flow through the cutaneous microcirculation of a patient with primary or secondary Raynaud's phenomenon. To reverse or lessen the cold induced or stress-induced vasoconstriction of the cutaneous arterial circulation in such patient, the $\alpha_{2C}$-AR antagonist is administered to the patient after exposure to the cold or to the stress. Such treatment serves to restore, at least partially, blood flow through the cutaneous arterial circulation of the treated patient.

In another embodiment, the method is used to reduce the extent of deleterious vasoconstriction that occurs in the small arteries, arterioles, and microcirculation of the lungs, heart, kidneys, skin, or gastrointestinal tract of a patient, particularly a scleroderma patient. The method comprises administering a therapeutically effective amount of an $\alpha_{2C}$-AR antagonist to a patient who is in need of the same. Such treatment serves to maintain or restore, at least in part, blood flow through the small arteries, arterioles, and microcirculation of the lungs, heart, kidneys, skin, and/or gastrointestinal tract in a such patient.

The present invention also provides methods and compositions for studying vasoconstriction in other disease states such as pulmonary hypertension, renal ischemia, gastrointestinal ischemia, and coronary ischemia hypertension, and for studying the physiology of vasoconstriction.

The present invention also relates to a pharmaceutical compositions comprising an $\alpha_{2C}$-AR antagonist and a pharmaceutically acceptable carrier.

DETAILED DESCRIPTION OF THE INVENTION

Figure 1:
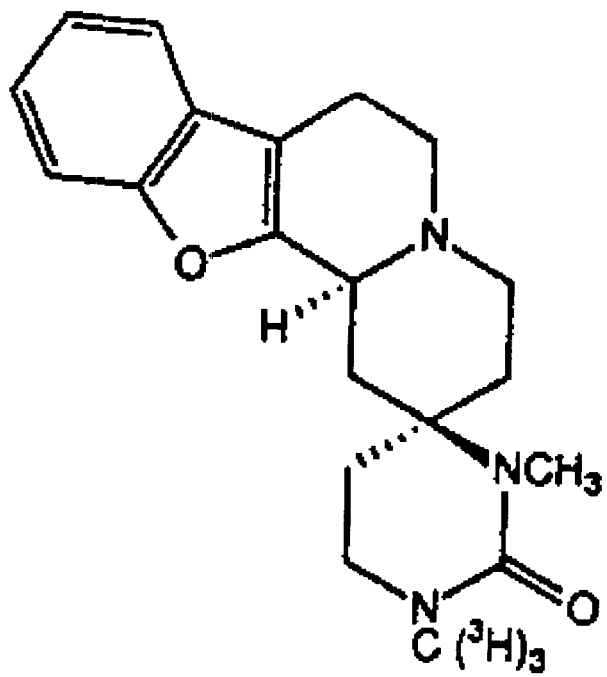
FIG. 1 shows the structure of the $\alpha_{2C}$-AR antagonist, MK 912.

The present invention provides methods of treating diseases which involve a deleterious vasoconstriction of the small arteries and/or arterioles of at least one organ or part of a patient's body. Such diseases include Raynaud's Phenomenon and scleroderma. Such methods comprise administering a therapeutically effective amount of an $\alpha_{2C}$-AR antagonist to a patient in need of the same. As used herein the term "$\alpha_{2C}$-AR antagonist" refers to a compound that selectively binds to an $\alpha_{2C}$ adrenergic receptor, i.e., the binding affinity of the compound to the $\alpha_{2C}$ adrenergic receptor is at least three times greater than the binding affinity of the compound to the $\alpha_{2A}$ adrenergic receptor or the $\alpha_{2B}$ adrenergic receptor. In other words, the $K_D$ of the antagonist and $\alpha_{2C}$-ARs is at least 3-fold lower than the $K_D$ of the antagonist and $\alpha_{2A}$-ARs or $\alpha_{2B}$-ARs. Furthermore, the $\alpha_{2C}$-AR antagonist, when given at the same concentration, has the ability to block the $\alpha_2$-AR-related response of vascular smooth muscle cells treated with an $\alpha_2$-AR agonist. Preferably, binding of the antagonist to the $\alpha_{2C}$-AR is reversible. Preferably, the antagonist is a competitive inhibitor of the $\alpha_2$-AR agonist. One example of a suitable $\alpha_{2C}$-AR antagonist is 1', 3'-dimethylspiro (1, 3, 4, 5', 6, 6', 7, 12b-octahydro-2H-benzo[b]furo[2,3-a) quinolizine-2,4'-pyrimidin-2'-one, which is available from Merck Chemical Company and has the structure shown in FIG. 1.

Unlike $\alpha_1$-ARs, functional $\alpha_2$-ARs are not widely distributed in the vascular system. $\alpha_2$-AR constrictor activity is not present in large arteries, but is generally restricted to small arteries/arterioles and to the venous circulation. $\alpha_2$-ARs are known to comprise three subtypes; $\alpha_{2A}$, $\alpha_{2B}$, and $\alpha_{2C}$. Although the $\alpha_2$-AR subtypes are highly homologous (50–60% amino acid identity), they are uniquely sensitive to physiological regulation. $\alpha_{2C}$-ARs have a predominantly intracellular distribution (endoplasmic reticulum and golgi apparatus) whereas $\alpha_{2A}$-AR are localized on the cell membrane. Furthermore, these receptor subtypes are reported to have differing sensitivities to desensitization and in their efficiency of coupling to G-proteins.

FORMULATION

The pharmaceutical composition comprises an $\alpha_{2C}$-AR antagonist and a pharmaceutically acceptable carrier. The term "pharmaceutically acceptable" means a non-toxic material that does not interfere with the effectiveness of the activity of the $\alpha_{2C}$-AR antagonist. The characteristics of the carrier will depend on the route of administration. The pharmaceutical composition, which comprises the $\alpha_{2C}$-AR antagonist and carrier, optionally further contains other agents which either enhance the activity of $\alpha_{2C}$-AR antagonist or complement its activity in treating the condition or disease. Optionally, additional factors and/or agents are included in the pharmaceutical composition to minimize side effects of the $\alpha_{2C}$-AR antagonist. Optionally, the pharmaceutical composition contains diluents, fillers, salts, buffers, stabilizers, solubilizers, antioxidants, preservatives and other materials which are conventionally used in pharmaceutical compositions.

Optionally, the pharmaceutical composition is in the form of a liposome in which $\alpha_{2C}$-AR antagonist is combined with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is conventional.

Routes of Administration

Administration of a pharmaceutical composition comprising the $\alpha_{2C}$-AR antagonist is carried out in a variety of conventional ways, such as oral ingestion, inhalation, topical application, or cutaneous, subcutaneous, intramuscular, intraperitoneal, parenteral or intravenous injection. For Raynaud's Phenomenom, local administration of a topical composition to the affected site or oral ingestion is preferred. For scleroderma or other diseases which involve deleterious vasoconstriction of the microcirculation of the lungs, kidneys, or gastrointestinal tract, the preferred route of administration is oral ingestion.

When the $\alpha_{2C}$-AR antagonist is administered orally, the pharmaceutical composition is, preferably, in the form of a tablet, capsule, powder, solution or elixir. When administered in tablet form, the pharmaceutical composition of the invention optionally contains a solid carrier such as a gelatin or an adjuvant. When administered in liquid form, a liquid carrier such as water, petroleum, oils of animal or plant origin such as peanut oil, mineral oil, soybean oil, or sesame oil, corn oil, or synthetic oils may be added. The liquid form of the pharmaceutical composition optionally contains physiological saline solution, dextrose or other saccharide solution, or glycols such as ethylene glycol, propylene glycol or polyethylene glycol.

When the $\alpha_{2C}$-AR antagonist is administered by intravenous, intramuscular, intraperitoneal, parenteral, cutaneous or subcutaneous injection, the pharmaceutical composition is in the form of a pyrogen-free, parenterally acceptable aqueous solution. The preparation of a parenterally acceptable aqueous solution, having suitable pH, isotonicity, and stability, is conventional. A preferred pharmaceutical composition for intravenous, intramuscular, cutaneous, or subcutaneous injection, preferably, contain, in addition to $\alpha_{2C}$-AR antagonist, an isotonic vehicle such as Sodium Chloride Injection, Ringer's Injection, Dextrose Injection, Dextrose and Sodium Chloride Injection, Lactated Ringer's Injection, or other vehicle.

Preferably, intravenous therapy is used when the patient, particularly the scleroderma patient, is in crisis. Intravenous administration, preferably, is continued until the crises subsides and the patient can be switched to oral administration. The duration of intravenous administration depends on the severity of the crises, the condition of the individual patient, and the response of each individual patient to the intravenous administration.

Dosage

The $\alpha_{2C}$-AR antagonist is administered to the patient in a therapeutically effective amount. As used herein, the term "therapeutically effective amount" means the total amount of $\alpha_{2C}$-AR antagonist that is sufficient to show a meaningful benefit, i.e., treatment, healing, prevention, reversal or amelioration of the condition or disease, or an increase in rate of treatment, healing, prevention or amelioration of such disease. The amount of $\alpha_{2C}$-AR antagonist administered to the patient depends upon the nature and severity of the condition being treated, the mode of administration, and on the nature of prior treatments which the patient has undergone. The dosages of $\alpha_{2C}$-AR antagonist used to treat the condition or disease are determined by running routine trials with appropriate controls. In such studies, varying dosages of the $\alpha_{2C}$-AR antagonist are administered indirectly to the subject or directly to the affected tissue or organ and the amount of antagonist sufficient to reduce, reverse, or prevent vasoconstriction and/or to improve blood flow through the small arteries, arterioles, and microcirculation of the affected digit or organ under conditions which cause restricted blood flow, such as cold or stress, is determined. Preferably, the dosage used is sufficient to return blood flow in the affected tissues or organs to levels comparable to those levels found in the same type of tissue or organ from control subjects, e.g., subjects that do not have Raynaud's Phenomenon or scleroderma. Preferably, the pharmaceutical composition contains from about 0.01 $\mu$g to about 100 mg, more preferably about 0.01 $\mu$g to about 10 mg, most preferably about 0.1 $\mu$g to about 1 mg of the $\alpha_{2C}$-AR per kg body weight.

Although a single dose of the $\alpha_{2C}$-AR antagonist may be sufficient to ameliorate the pathological effect of the condition or disease and to return blood flow levels to normal or near normal, it is expected that multiple doses of the $\alpha_{2C}$-AR antagonist will be administered to the patient, particularly to patients with scleroderma.

Population Receiving Treatment

The $\alpha_{2C}$ AR antagonist is administered to a patient who has exhibited symptoms of or has been diagnosed with a disease or condition associated with a deleterious vasoconstriction of one or more parts or organs of the patient's body. In the case of Raynaud's Phenomenon, the $\alpha_{2C}$-AR antagonist is administered to a patient diagnosed as having Raynaud's Phenomenon before or after the patient is exposed to the cold or emotional stress. In the case of scleroderma, administration of the antagonist, preferably, is begun as soon as possible following diagnosis. Preferably the $\alpha_{2C}$-AR antagonist is administered to such patients throughout their lifetime in order to prevent further lesions or deleterious changes to the affected or involved organs.

EXAMPLES

The following examples are for purposes of illustration only and are not intended to limit the scope of the invention as defined in the claims which are appended hereto.

Example 1

Inhibition of Cold-Augmented Vasoconstriction of Cutaneous Arteries by an $\alpha_{2C}$-AR Antagonist To determine the role of $\alpha_2$-AR subtypes in cold-induced vasoconstriction and the effect of selective $\alpha_2$-AR antagonists on this phenomenon, a new model of the cutaneous circulation, namely the mouse tail artery, was used.

Methods and Materials

Blood Vessel Chamber

Male mice (C57BL6) were euthanized by $CO_2$ asphyxiation. Proximal and/or distal segments of tail artery were then rapidly removed and placed in cold Krebs-Ringer bicarbonate solution (in mM): 118.3 NaCl, 4.7 KCl, 1.2 $MgSO_4$, 1.2 $KH_2PO_4$, 2.5 $CaCl_2$, 25.0 $NaHCO_3$, 11. glucose (control solution). The small arteries were cannulated at both ends with glass micropipettes, secured using 12-0 nylon monofilament suture and placed in a microvascuiar chamber (Living Systems, Burlington, Vt.). The arteries were maintained at a constant transmural pressure of 60 mmHg in the absence of flow. The chamber was superfused with control solution and maintained at 37° C., pH 7.4, and gassed with 16% $O_2$-5% $CO_2$-balance $N_2$. The chamber was placed on the stage of an inverted microscope (X20, Nikon TMS-F, Japan) connected to a video camera (Panasonic, CCTV camera, Japan). The vessel image was projected onto a video monitor and the internal diameter continuously determined by a video dimension analyzer (Living Systems Instrumentation, Burlington Vt.) and monitored using a BIOPAC (Santa Barbara, Calif.) data acquisition system (Gateway Dimensions Pentium Computer).

Protocol

Small arteries were allowed to equilibrate for 30–40 min at a transmural pressure (PTM) of 60 mmHg before addition of $\alpha_1$ and $\alpha_2$-AR agonists and antagonists. Concentration-effect curves to the selective $\alpha_1$-AR agonist, phenylephrine, or the selective $\alpha_2$-AR agonist, UK 14,304 (brimonidine, 5-bromo-N-(4,5-dihydro-1H-imidazol-2-yl)-6-quinoxalinamine) were generated by increasing the concentration of the agonists in half-log increments, once the constriction to the previous concentration had stabilized. Following completion of the concentration-effect curve, the influence of the agonists was terminated by repeatedly exchanging the buffer solution and allowing the artery to return to its stable baseline level.

To evaluate the effect of selective $\alpha_2$-AR antagonists on vasoconstriction, concentration-effect curves to UK 14,304 were determined under control conditions and in the presence of the selective $\alpha_{2A}$-AR antagonist, BRL 44408 (100 and 1000 nM), the selective $\alpha_{2B}$-AR antagonist ARC 0239 (50 nM) or the selective $\alpha_{2C}$-AR antagonist MK 912 (0.3 nM) (Table 1). When these receptor antagonists were used, the preparations were incubated for 30 min with the drugs prior to, and also during, exposure of the arteries to the agonists. When analyzing the influence of cold on $\alpha$-AR responsiveness, the temperature of the superfusate was decreased to 28° C. for 30 min prior to commencing a concentration effect curve to the constrictor agonists. This provides sufficient time for the effect of cold on adrenergic reactivity to stabilize.

Drugs

ARC 0239 was a gift from Boehringer Ingelheim (Ridgefield, Conn.), BRL 44408 was a gift from SmithKline Beecham (Harlow, UK), MK 912 was a gift from Merck (West Point, Pa.), phenylephrine and sodium nitroprusside were obtained from SIGMA (St. Louis, Mo.) and UK 14,304 was from Research Biochemicals International (Natick, Mass.). Stock solutions of drugs were prepared fresh each day and stored at 4° C. during the experiment. Drugs were dissolved in distilled water with the exception of i) UK 14,304 which was dissolved in DMSO (highest chamber concentration of 0.001%), ii) BRL 44408 which was dissolved in 0.1 N HCI (highest chamber concentration of 0.04%), iii) ARC 0239 which was dissolved in methanol (highest chamber concentration of 0.004%). At these concentrations, the solvents did not alter reactivity of the blood vessels. All drug concentrations are expressed as final molar concentration (M, moles/liter) in the chamber superfusate.

Data Analysis

Vasomotor responses were expressed as a percentage change in internal diameter (ID) prior to administrating the agent. Because of the phasic behavior of the vasomotion in distal. tail arteries, the signal was electronically averaged (BIOPAC software, smoothing factor of 2000) in order to obtain diameter measurements. Functional data is expressed as means±SEM for n number of experiments, where n equals the number of animals from which blood vessels were studied. Antagonist dissociation constants ($K_D$) were determined either from Arunlakshana and Schild plots or according to the formula: $K_D$=[Ant]/(CR-1), where [Ant] is the concentration of antagonist, and CR the ratio of agonist-concentrations producing equal responses in the presence and absence of the antagonist. In all cases, slopes of Arunlakshana and Schild plots were not significantly different from unity, consistent with competitive antagonism. Statistical evaluation of the data was performed by Student's t-test for either paired or unpaired observations. When more than two means were compared, analysis of variance was used. If a significant F value was found, Scheffe's test for multiple comparisons was employed to identify differences among groups. Values were considered to be statistically different when P was less than 0.05.

Results

Baseline Characteristics

Figure 2:
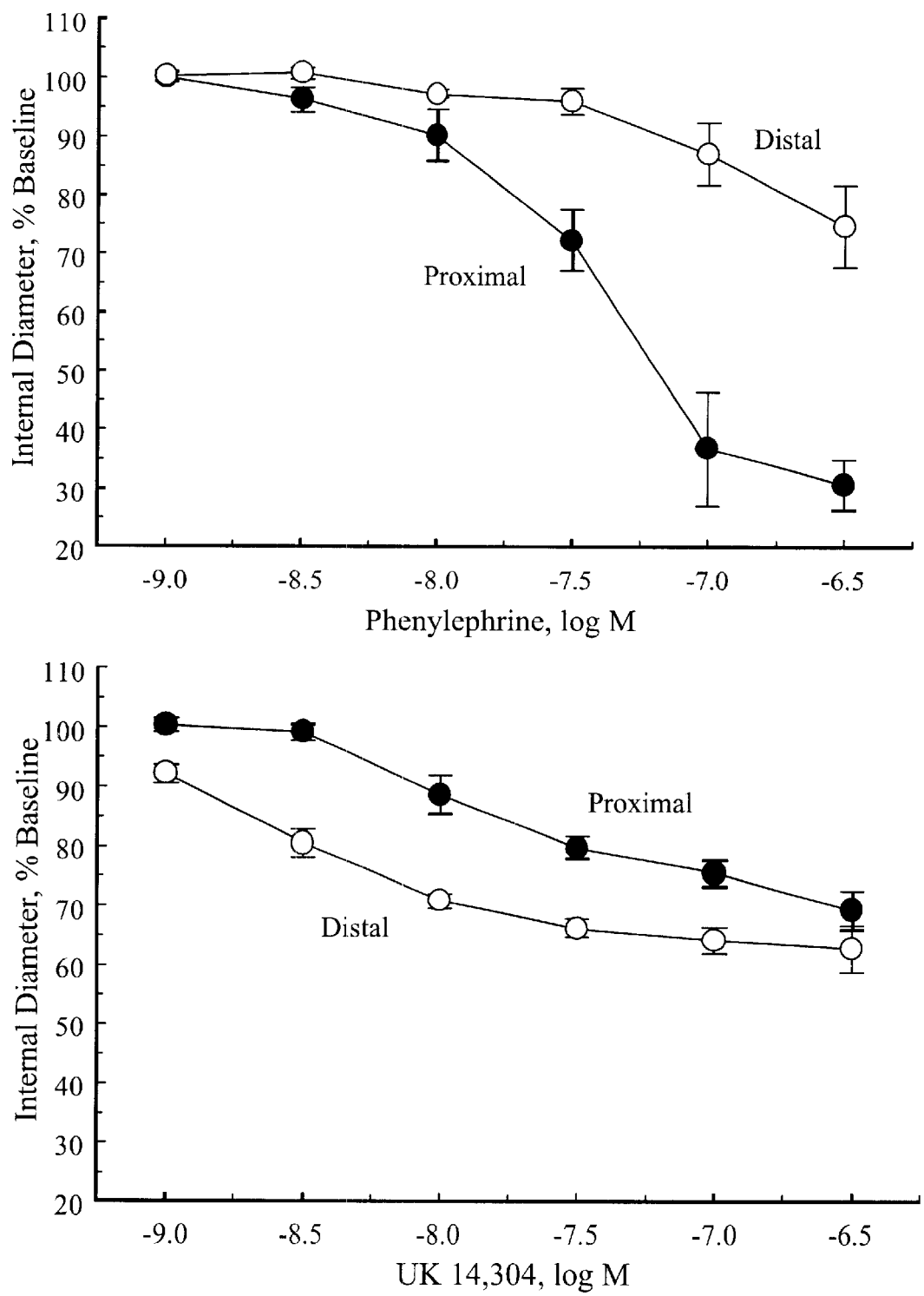
FIG. 2 shows the vasoconstrictor effects of the selective $\alpha_1$-AR agonist, phenylephrine ($10^{-9}$ to $3\times10^{-7}$M), or the selective $\alpha_2$-AR agonist, UK 14,304 ($10^{-9}$ to $3\times10^{-7}$M), in proximal and distal tail arteries of the mouse. Vasoconstriction was expressed as a percentage of the stable baseline diameter and is presented as means±SEEM (n=4 [UK 14,304] or 3 [phenylephrine]).

When transmural pressure ($P_{TM}$) was increased from 10 mmHg to 60 mmHg, distal segments of the mouse tail artery immediately dilated and then gradually constricted. The pressure-induced constriction or myogenic response comprised both tonic and phasic components. Administration of the vasodilator, sodium nitroprusside ($10^{-5}$M), abolished both constrictor components. Under these conditions, an increase in transmural pressure caused only a passive increase in arterial diameter (FIG. 2). In contrast to the distal segments, proximal segments of the mouse tail artery did not constrict in response to increases in $P_{TM}$ and, under quiescent conditions did not dilate to sodium nitroprusside ($10^{-5}$ M), indicating the absence of myogenic tone. These responses are characteristic of arterioles. Once the blood vessels had stabilized at 60 mmHg, the internal diameter (ID) was 333.7±9.0μ (n=5) in proximal and 157.8±14.8p (n=5) in distal segments of the mouse tail arteries.

$\alpha_1$ and $\alpha_2$-AR Activation

Stimulation of $\alpha_1$-ARs by phenylephrine ($10^{-9}$ to $3\times10^{-7}$ M) or $\alpha_2$-ARS by UK 14,304 ($10^{-9}$ to $3\times10^{-7}$M) caused concentration-dependent constriction of the proximal and distal segments of the mouse tail arteries (FIG. 2). Distal segment were significantly more responsive to $\alpha_2$-AR activation but significantly less responsive to activation of $\alpha_1$-ARs, compared to proximal segments (FIG. 2). Thus, the constrictor activity of $\alpha_2$-ARs increased in distal compared to proximal segments, whereas the opposite pattern was observed for $\alpha_1$-ARs. These are similar to results observed in human digital circulation. These results are consistent with previous reports that constrictor $\alpha_{2A}$-ARs are functional in the microcirculation, whereas in large arteries, the receptors are expressed but not functional.

Influence of Cold on $\alpha$-AR Constriction

Figure 3:
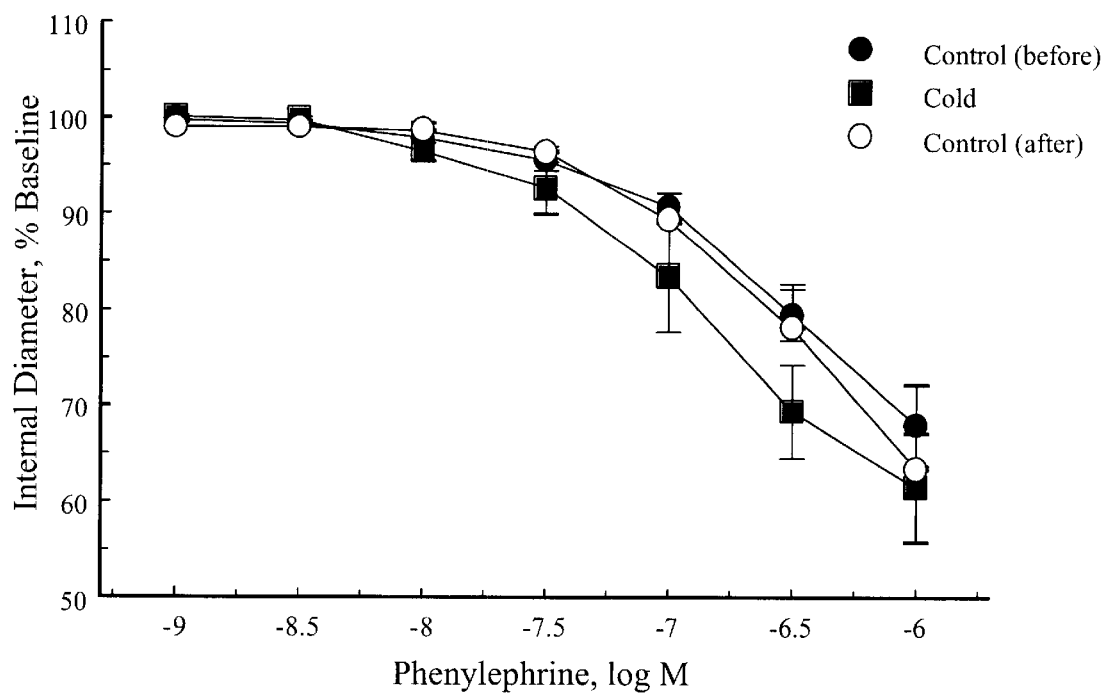
FIG. 3 shows the effect of cold (from 37° C. to 28° C.) on the vasoconstrictor response to the selective $\alpha_1$-AR agonist, phenylephrine ($10^{-9}$ to $10^{-6}$M), in distal tail arteries of the mouse. Vasoconstriction was expressed as a percentage of the stable baseline diameter and is presented as means±SEM (n=4).
Figure 4:
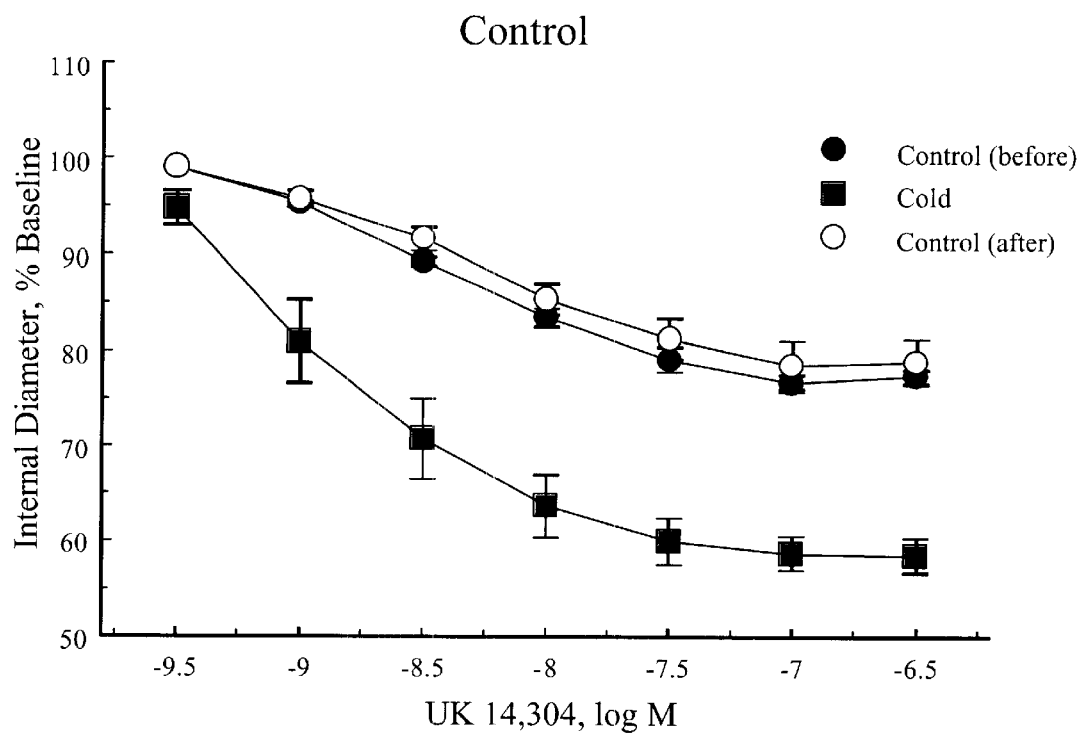
FIG. 4 shows the effect of cold (from 37° C. to 28° C.) on the vasoconstrictor response to the selective $\alpha_2$-AR agonist, UK 14,304 ($10^{-9}$ to $3\times10^{-7}$M), in distal tail arteries of the mouse. Vasoconstriction was expressed as a percentage of the stable baseline diameter and is presented as means±SEM (n=4).

The influence of cold on adrenergic constrictor responsiveness was evaluated on distal segments. Cold did not significantly affect the baseline diameter or myogenic tone in distal segments of the mouse tail arteries (IDs of 153±12.48 and 157.9±14.6p, at 37° C. and 28° C., respectively, n=8). Furthermore, cold did not affect the constrictor response to stimulation of $\alpha_1$-ARs by phenylephrine (FIG. 3). However, cold dramatically and reversibly increased the vasoconstriction caused by activation of $\alpha_2$-ARs with UK 14,304 (FIG. 4).

Cold and $\alpha_2$-AR Subtypes

Figure 5:
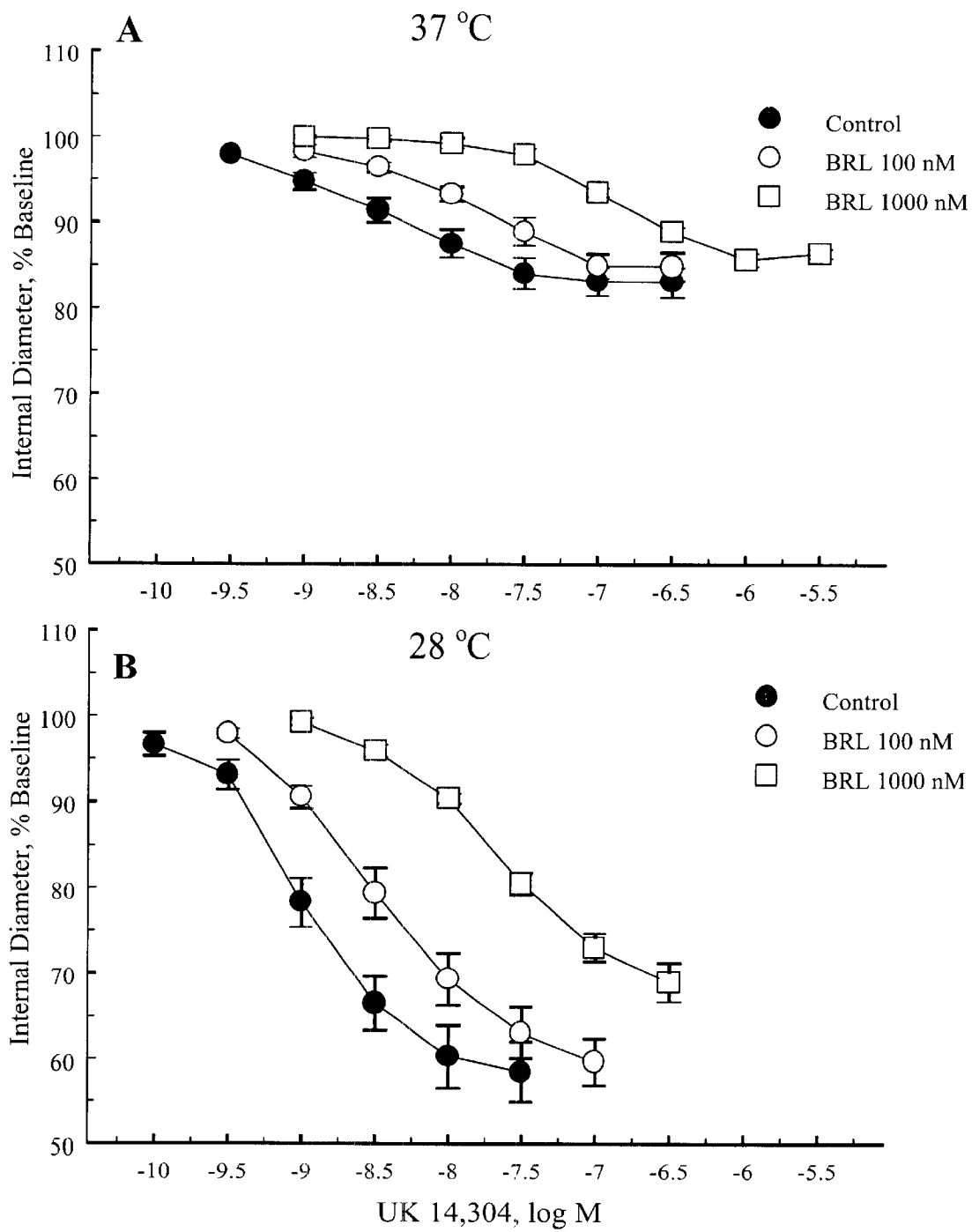
FIG. 5 shows the effect of the $\alpha_{2A}$-AR antagonist, BRL 44408 (100 and 1,000 nM), on the vasoconstrictor response to the $\alpha_2$-AR agonist, UK 14,304 ($10^{-9}$ to $3\times10^{-7}$M), in distal tail arteries of the mouse. Inhibitory effect of BRL 44408 was assessed at 37° C. (warm, upper panel) and at 28° C. (cold, lower panel). Vasoconstriction was expressed as a percentage of the stable baseline diameter and is presented as means±SEM (n=4). Absence of error bar indicates the SEM was less than the size of the symbol.
Figure 6:
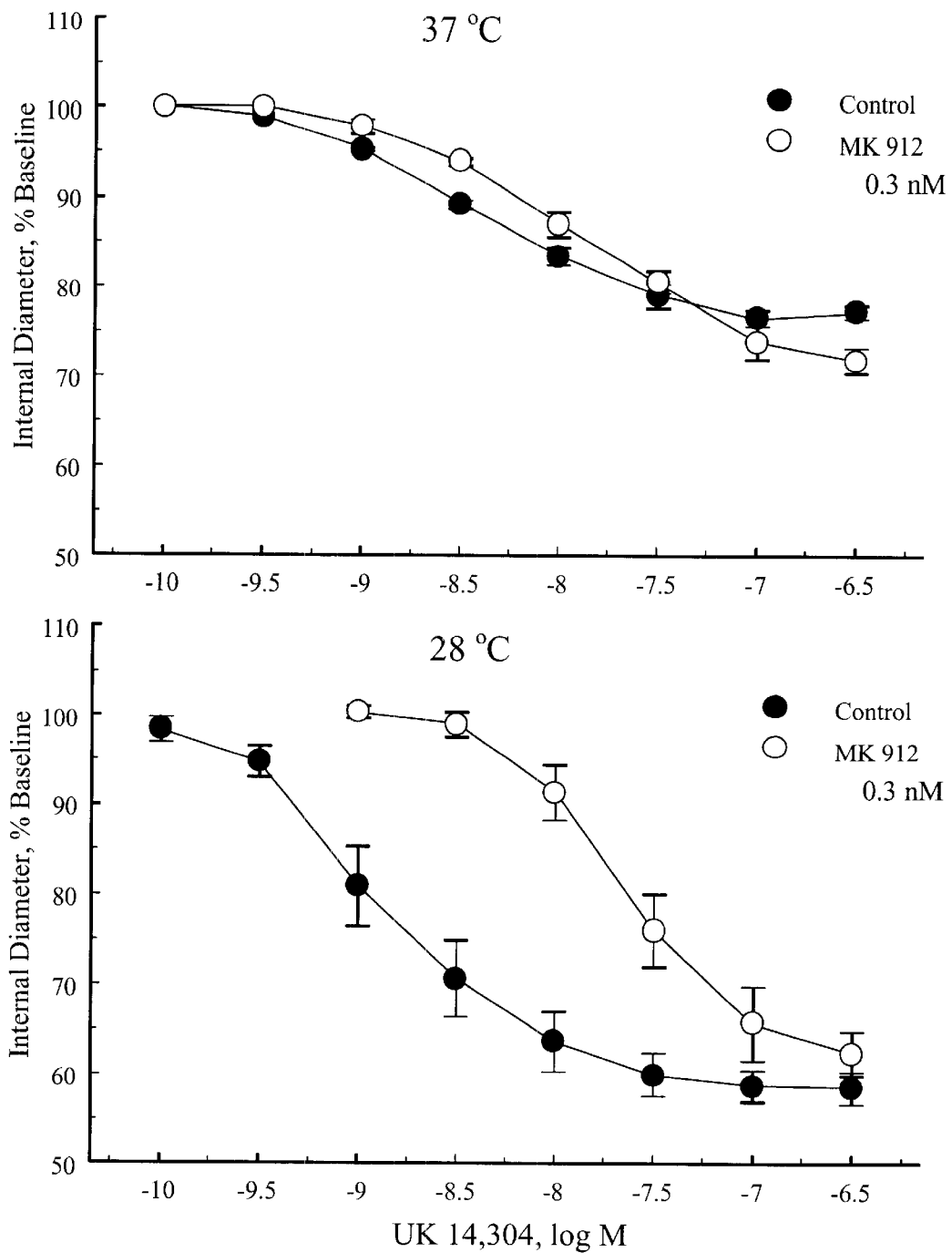
FIG. 6 shows the effect of the $\alpha_{2C}$-AR antagonist, MK 912 (0.3 nM), on the vasoconstrictor response to the $\alpha_2$-AR agonist, UK 14,304 (10–9 to $3\times10^{-7}$M), in distal tail arteries of the mouse. Inhibitory effect of MK 912 was assessed at 37° C. (warm, upper panel) and at 28° C. (cold, lower panel). Vasoconstriction was expressed as a percentage of the stable baseline diameter and is presented as means±SEM (n=4).

At warm temperatures, vasoconstriction to the $\alpha_2$-AR agonist UK 14,304 was inhibited by the selective $\alpha_{2A}$-AR antagonist BRL 44408 (100 nM and 1000 nM) (FIG. 5), but not inhibited by the selective $\alpha_{2B}$-AR antagonist ARC 239 (50 nM) (data not shown) or the selective $\alpha_{2C}$-AR antagonist MK 912 (0.3 nM) (FIG. 6). Based on the dissociation constants ($K_D$) for ARC 239 and MK 912 (Table 1), these antagonists would be expected to cause ~10-fold and ~6-fold shifts in concentration-effects curves generated by $\alpha_{2B}$-AR and $\alpha_{2C}$-AR stimulation, respectively. The Arunlakshana and Schild plot or the inhibitory effect of BRL 44408 generated a −log $K_D$ of 7.69±0.13 ($K_{D \, of}$ 20 nM, n=4), consistent with antagonism of $\alpha_{2A}$-ARs (table 1). These results indicate that, at warm temperatures, $\alpha_{2A}$-ARs but not $\alpha_{2B}$-ARs or $\alpha_{2C}$-ARs contribute to $\alpha_2$-AR vasoconstriction.

Figure 7:
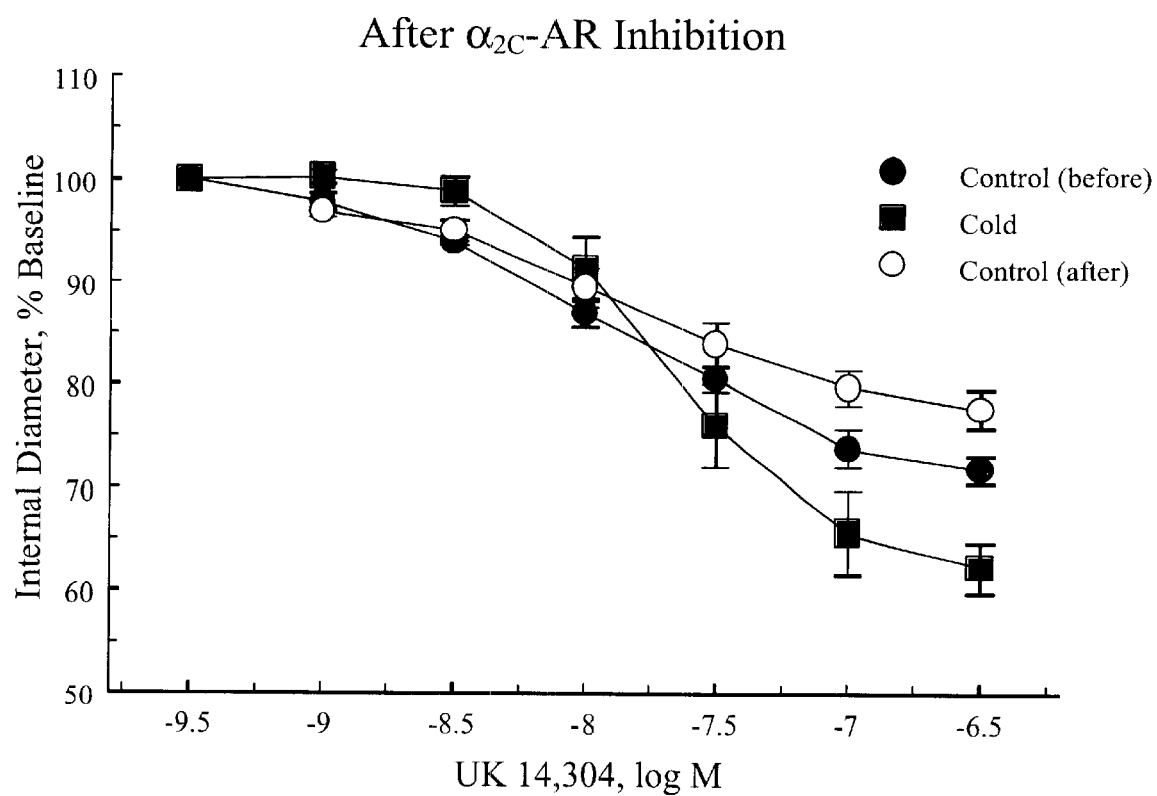
FIG. 7 shows the effect of the $\alpha_{2C}$-AR antagonist, MK 912 (0.3 nM), on cold-induced augmentation of $\alpha_2$-AR vasoconstriction in distal tail arteries of the mouse. Vasoconstrictor responses to the $\alpha_2$-AR agonist, UK 14,304 ($10^{-9}$ to $3\times10^{-7}$M) were assessed as described in FIG. 4. However, in contrast to FIG. 4, $\alpha_{2C}$-AR s were blocked by treating the arteries with MK 912 (0.3 nM) before and during each of the concentration effect curves. Vasoconstriction was expressed as a percentage of the stable baseline diameter and is presented as means±SEM (n=4).

During exposure to cold, the augmented vasoconstrictor response to UK 14,304 was dramatically inhibited by the $\alpha_{2C}$-AR antagonist MK912 ($3\times10^{-10}$M) (FIG. 6). The inhibitory effect generated a −log $K_D$ value of 10.9±0.17 ($K_D$ of 14 pM, n=4), consistent with inhibition of $\alpha_{2C}$ARs (Table 1). Inhibition of $\alpha_{2C}$-ARs attenuated the $\alpha_2$-AR-induced vasoconstriction only at low temperatures. Thus the $\alpha_{2C}$-AR antagonist, MK 912, selectively abolished cold-induced amplification of the $\alpha_2$-AR response (FIG. 7).

The $\alpha_2$-AR-induced vasoconstrictor response which occurred at 28° C. was not inhibited by the $\alpha_{2B}$-AR antagonist ARC 0239 (50 nM, data not shown), but was reduced by the $\alpha_{2A}$ antagonist BRL 44408 (100 and 1000 nM) (FIG. 5). The Arunlakshana and Schild plot for the inhibitory effect of BRL 44408 generated a −log $K_D$ of 7.54+0.10 ($K_D$ value of 29 nM, n=4), which was not significantly different from that observed at 37° C. Thus, blockade of $\alpha_{2A}$-ARs with BRL 44408 inhibited $\alpha_2$-AR-induced constriction to a similar degree at warm and cold temperatures, and did not reduce the, cold-induced amplification of the response (compare the concentration-effect curves in FIG. 6).

TABLE 1

$K_D$ values (in nM) for $\alpha_2$-AR antagonists

| | $\alpha\text{-}2A^A$ | $\alpha\text{-}2B^A$ | $\alpha\text{-}2C^A$ | Mouse Tail Artery | |
|---|---|---|---|---|---|
| | | | | 37° C. | 28° C. |
| BRL44408 ($\alpha$-2A) | 13 | 174 | 187 | 20 | 29 |
| ARC239 ($\alpha$-2B) | 256 | 4.6 | 51 | >50 | >50 |
| MK912 ($\alpha$-2C) | 1.8 | .33 | 0.045 | >0.3 | >0.014 |

[A]Data from Flavahan, N. A., T. J. Rimele, J. P. Cooke, and P. M. Vanhoune. 1984. Characterization of postjunctional alpha-1 and alpha-2 adrenoceptors activated by exogenous or nerve-released norepinephrine in the canine saphenous vein. *J Pharmacol Exp Ther.* 230 (3):699–705; Harker, C. T., and P. M. Vanhoutte. 1988. Cooling the central ear artery of the rabbit: myogenic and adrenergic responses. *J Pharmacol Exp Ther* 245 (1):89–93; anal Faber, J. E. 1988. Effect of local tissue cooling on microvascular smooth muscle and postjunctional alpha 2-adrenoceptors. *Am J Physiol.* 255 (1 Pt 2):H121–30.

These results confirm that $\alpha_{2C}$-ARs do not normally contribute to vasoconstriction. However, during cold-induced vasoconstriction, $\alpha_{2C}$-ARs are no longer silent and mediate the remarkable cold-induced augmentation of $\alpha_2$-AR responsiveness. These results also indicate that $\alpha_{2C}$-AR antagonists can be used to relieve the vasospastic episodes that occur when individuals with Raynaud's Disease are exposed to cold or stress. Because $\alpha_{2C}$-AR appear to be silent in the normal regulation of vascular function, selective blockade of these receptors with an $\alpha_{2C}$-AR antagonist is expected to provide a highly selective therapeutic intervention for this condition.

Example 2
Effect of $\alpha_{2C}$-AR Antagonists on the Vascular Smooth Muscle Cells of Patients with Scleroderma Materials and Methods
Subject Characteristics Skin biopsies (6 mm punch) were obtained from the same location on the medial aspect on the upper arm of patients and control subjects. Eleven patients with diffuse cutaneous SSc were studied: nine female and two male. Their average age was 49 years old (range 33 to 69) and they had SSc for an average of 4 years (range 1 to 9 years from first physician diagnosis of SSc). SSc patients were recruited from the Johns Hopkins and University of Maryland Scleroderma Center. All patients met the American College of Rheumatology criteria for a diagnosis of SSc. Biopsy of the skin was performed in the upper arm in an area considered to have normal skin thickness determined by clinical palpation (clinically-uninvolved skin). Patients with overlap syndromes (e.g. lupus) were excluded. Patient medications varied between individuals: anti-inflammatory /immunosuppressant, 4 patients on prednisone, 1 on methotrexate, 1 on cyclophosphamide, and 1 on D-penicillamine; gastrointestinal, 5 on omeprazole, 3 on cisapride, 2 on ranitidine, 1 on lansoprazole; angiotensin converting enzyme inhibitors, 3 on enalapril, 1 on lisinopril; angiotensin receptor antagonists, 1 on losartin, 1 on valsartin; calcium antagonists, 2 on nifedipine, 1 on verapamil, 1 on amlodipine, 1 on diltiazem; $\alpha_1$-adrenergic receptor antagonists, 1 on terazosin. Vasoconstrictor responses to the $\alpha_1$-adrenergic receptor ($\alpha_1$-AR) agonist, phenylephrine, were not included for the patient receiving terazosin. Eight normal subjects were analyzed: six female and two males with an average age of 50 years old (range 38 to 62). All patients and volunteers gave informed consent and the study was approved by the Johns Hopkins University human subjects IRB committee.

Blood Vessel Preparation

Arterioles were dissected from the deep dermal plexus of the biopsies and any side branches tied. Subsequent histological examination revealed no structural abnormalities in SSc arterioles. The arterioles were cannulated with glass micropipettes and placed in a microvessel chamber as previously describe. The arterioles were maintained in no-flow state at a constant transmural pressure ($P_{TM}$)of 40 mmHg. The chamber was superfused with buffer solution (37° C., pH 7.4, gassed with 16% $O_2$-5% $CO_2$-balance $N_2$) and placed on stage of an inverted microscope for continuous monitoring of internal diameter using a video camera and video dimension analyzer.

Experimental Protocol

Vasoconstriction was assessed in response to: i) KCl (15 to 60 mM), ii) the selective $\alpha_1$-AR agonist, phenylephrine (0.01 to 1 $\mu$M) (SIGMA, St Louis, Mo.), or iii) the selective $\alpha_2$-AR agonist, UK 14,304 (1 to 100 nM) (brimonidine, 5-bromo-N-(4,5-dihydro-1H-imidazol-2-yl)-6-quinoxalinamine, RBI, Natick, Mass.). Responses to UK 14,304 were also evaluated following denudation of the endothelium, achieved by carefully placing a wire (70$\mu$diameter) through the vessel lumen. Endothelium-removal was confirmed by histology and by loss of response to the endothelial stimuli acetylcholine or bradykinin.

Data Analysis

Responses were expressed as a percentage change in baseline diameter. Data is expressed as means±SEM for n number of experiments, where n equals the number of subjects from which blood vessels were studied. Concentration-effect curves were analyzed by comparing: i) maximal responses (vasoconstriction or dilatation), and ii) the area under the curve (AUC). Statistical evaluation of the data was performed using paired or unpaired t-tests. Responses were considered to be statistically different when P was less than 0.05.

Results
Baseline Characteristics

At a $P_{TM}$ of 40 mmHg, there was no significant difference in the diameter of control and SSc arterioles (164±15$\mu$ and 166±18$\mu$, respectively). The arterioles did not display spontaneous constrictor activity, and administration of vasodilator agonists (e.g. papaverine, 10 $\mu$M; sodium nitroprusside, 10 $\mu$M) did not cause relaxation in unstimulated arterioles.

Constrictor Agonists

Figure 8:
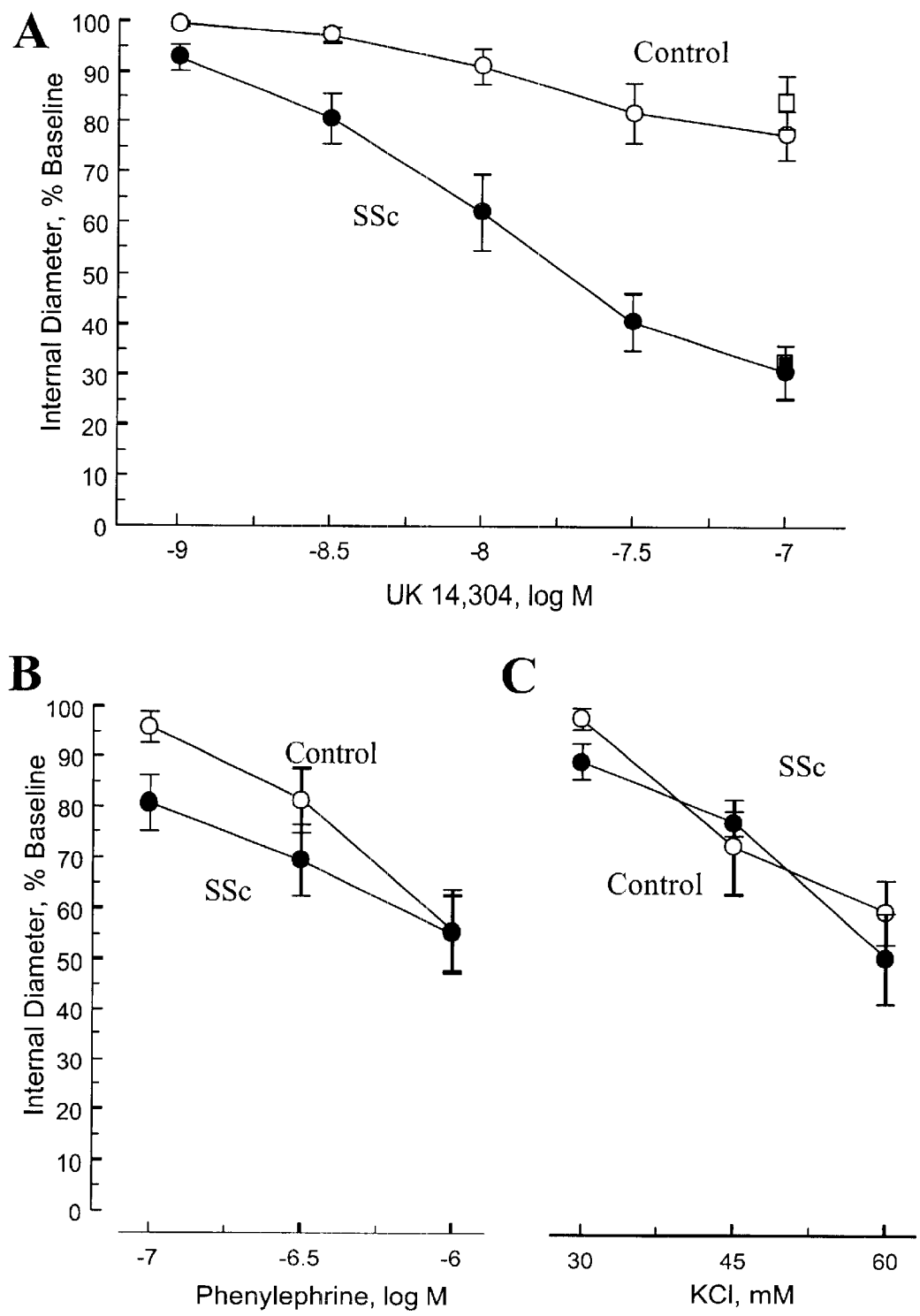
FIG. 8 shows the vasoconstrictor responses evoked by the selective $\alpha_2$-AR agonist UK 14,304 (panel A) the selective $\alpha_1$-AR agonist phenylephrine (panel B), or the receptor-independent stimulus KCl (panel C) in control and SSc arterioles. Concentration-effect curves were obtained in arterioles with endothelium (circles). In addition, the response to UK 14,304 (100 nM, log M of –7) is also presented for endothelium-denuded arterioles (squares). Empty symbols, control; filled symbols, SSc. Concentration is expressed as the molar concentration (moles/liter, M) of the agonist in the solution and presented as log M. SSc arterioles had increased reactivity to $\alpha_2$-AR stimulation demonstrated by an increased maximal response to the agonist (P=0.000014) and increased AUC (P<0.00037). In contrast, constrictor responses to KCl or to the $\alpha_1$-AR agonist, phenylephrine were not significantly different between control and SSc arterioles (KCl maximal observed response 60 mM: P=0.44, AUC: P=0.36; Phenylephrine maximal observed response 1 $\mu$M: P=0.87, AUC: P=0.23)

The $\alpha_2$-AR agonist, UK 14,304 (1–100 nM) caused concentration-dependent constriction that was increased in SSc compared to control arterioles (FIG. 8). The increased reactivity was associated with an increased maximal response to the agonist (25±5% and 67±4% constriction in control and SSc arterioles, respectively; P=0.000014). In contrast, constrictor responses to KCl (15 to 60 mM), a receptor-independent, smooth muscle stimulus were similar in control and SSc arterioles. Likewise, constriction evoked by the $\alpha_1$-AR agonist, phenylephrine (0.01 to 1 $\mu$M) was not significantly different between control and SSc arterioles, with 1 $\mu$M of the agonist causing constriction of 45±8% and 45±7% in control and SSc arterioles, respectively (FIG. 8).

Because increased constriction can result from diminished activity of endothelial dilator mechanisms, the constrictor response to $\alpha_2$-AR activation was also evaluated following mechanical denudation of the endothelium. The vasoconstrictor activity of UK 14,304 was not affected by endothelial denudation (FIG. 8) (maximal responses of 25±7% and 67±10% constriction in endothelium-denuded, control and SSc arterioles, respectively).

Figure 9:
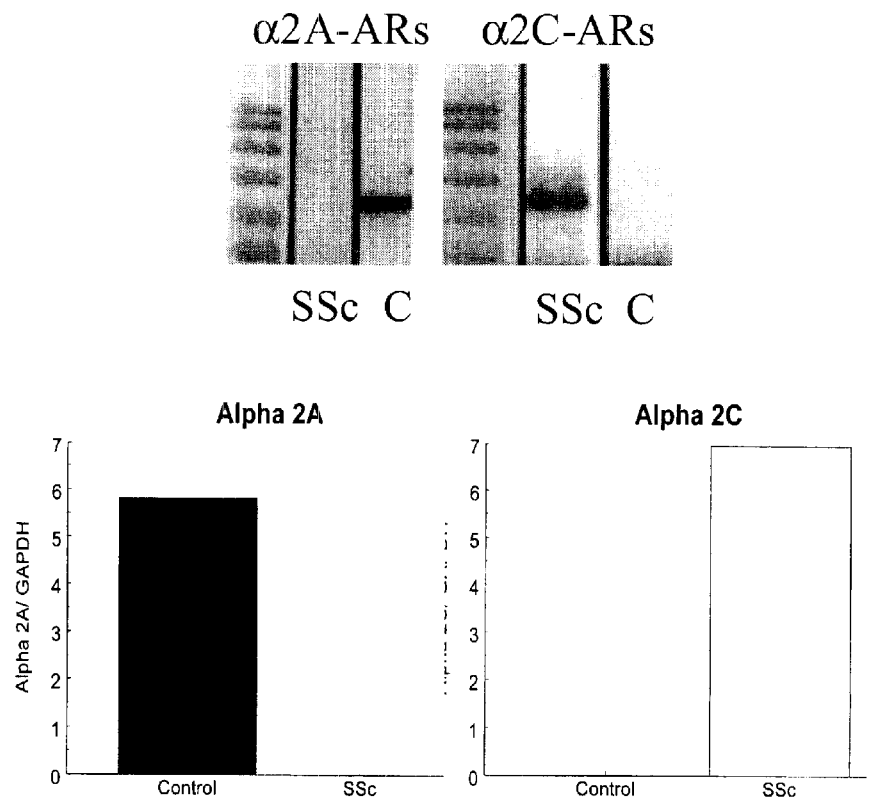
FIG. 9 shows the levels of mRNA molecules encoding the $\alpha_{2A}$ and the $\alpha_{2C}$ adrenergic receptors in the dermal arteries of healthy control subjects and patients with scleroderma.

These results demonstrate that arterioles isolated from clinically-uninvolved skin of diffuse SSc subjects have a selective increase in the reactivity of smooth muscle $\alpha_2$-ARs. SSc arterioles did not display spontaneous vasospastic activity in the absence of stimulation, and had normal vasoconstrictor activity in response to KCl or to activation of smooth muscle $\alpha_1$-ARs. Therefore, SSc arterioles do not have a generalized defect in vasomotor regulation. In addition to smooth muscle constrictor $\alpha_2$-ARs, $\alpha_2$-ARs can also be present on endothelial cells, with activation leading to increased production of NO and dilatation in some blood vessels. Increased constriction to $\alpha_2$-AR stimulation in SSc arterioles could therefore reflect endothelial dysfunction or injury. However, endothelial dilator function, assessed with acetylcholine and bradykinin, was similar in control and SSc arterioles. Furthermore, $\alpha_2$-AR constrictor activity was not altered by endothelial denudation, indicating that the increased $\alpha_2$-AR reactivity results from selective enhancement of vascular smooth muscle $\alpha_2$-AR signaling To determine whether this increased responsiveness resulted from altered or enhanced expression of a particular subtype of $\alpha_2$ adrenergic receptor, RT-PCR was performed on RNA obtained from the dermal arteries of patients with scleroderma and healthy control subjects. The RT-PCR employed primers which are specific to the genes encoding $\alpha_{2A}$ and $\alpha_{2C}$ receptors and used standard techniques. As shown in FIG. 9, the dermal arterioles of healthy, control subjects express mRNA encoding the $\alpha_{2A}$ receptor but lack mRNA encoding the $\alpha_{2C}$ adrenergic receptor. In contrast, dermal arterioles from the uninvolved skin of scleroderma patients lack mRNA which encodes the $\alpha_{2A}$ adrenergic receptors, but contain significant amounts of mRNA which encode the $\alpha_{2C}$ adrenergic receptors. It is believed that this switch in expression from the $\alpha_{2A}$ adrenergic receptors to the $\alpha_{2C}$-adrenergic receptor is the cause of the increased reactivity of the $\alpha_2$ adrenergic receptors and the underlying vasculopathy in scleroderma.

To determine the effect of selective $\alpha_2$ AR agonists and antagonists on vasoconstriction, small dermal arteriesларteрioles from healthy controls and from SSc subjects were obtained and analyzed using the microperfusion system described above. In order to determine the influence of $\alpha_{2C}$-AR blockade, paired arteries from each subject were used. In one artery of each pair, responses to UK 14,304 were determined repeatedly to demonstrate that the response to UK 14,304 remained constant with repeated exposure (time control). Indeed, in both control and SSc arteries, the response to UK 14,304 was reproducible. In the other artery of each pair, increasing concentrations of the $\alpha_{2C}$-AR antagonist (MK 912) was administered before the response to UK 14,304 was determined.

Figure 10:
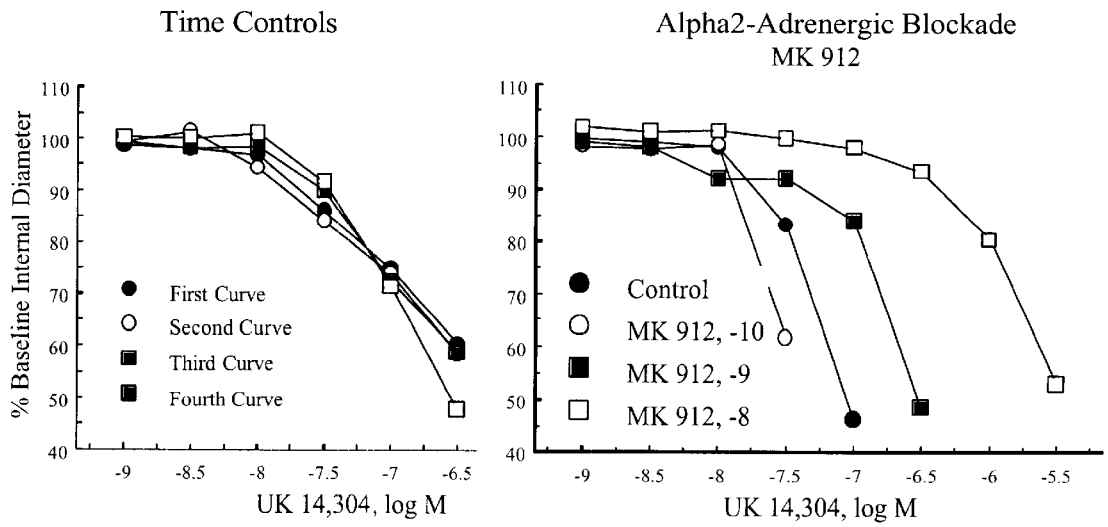
FIG. 10 shows the effect of the $\alpha_{2C}$-AR antagonist, MK 912 (0.3 nM), on the vasoconstrictor response to the $\alpha_2$-AR agonist, UK 14,304 ($10^{-9}$ to $3\times10^{-7}$M), in dermal arteries of healthy control subjects and patients with scleroderma.
Figure 10:
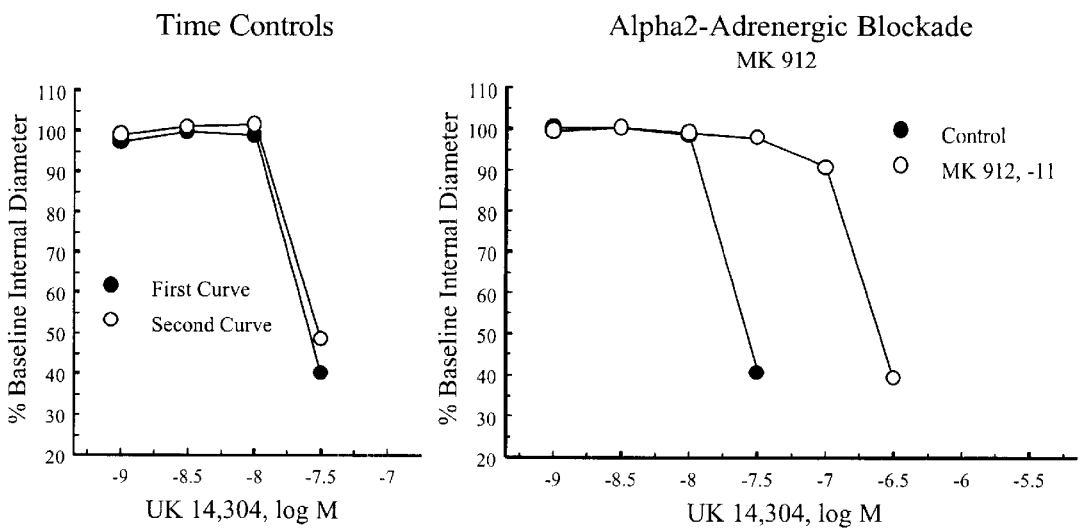

The results demonstrated that extremely low concentrations of the $\alpha_{2C}$-AR inhibitor MK 912 (e.g. $10^{-11}$M) reduced the vasoconstrictor response to α2-AR stimulation in SSc but not in control arteries. (FIG. 10). This confirms that blockade of $\alpha_{2C}$-AR is capable of reducing the abnormal vasoconstrictor activity of SSc blood vessels. Indeed, the calculated dissociation constant for MK 912 (–log Kb of 11.91) confirmed that it was acting to inhibit $\alpha_{2C}$-ARs. Much higher concentrations of MK 912 (i.e. $10^{-9}$M or 100-fold higher) were needed to inhibit responses to UK 14,304 in control arteries. At these concentrations, MK 912 is no longer selective for $\alpha_{2C}$-ARs, and the calculated dissociation constant (–log Kb of 9.33) confirmed that the antagonist was acting to inhibit $\alpha_{2A}$-ARs. Therefore, the functional data is in agreement with the RT-PCR data and indicates that there is a switch in receptor expression from $\alpha_{2A}$-ARs on control arteries to $\alpha_{2C}$-ARs in scleroderma. It also indicates that $\alpha_{2C}$-AR antagonists inhibit the abnormally high vasoconstrictor activity in scleroderma, and thereby, reverse the disease process in vitro.

What is claimed is:

1. A method of treating a patient with a condition that involves vasoconstriction of the small arteries or arterioles of a part or organ of the patient's body, comprising:
    administering to the patient a therapeutically effective amount of an $\alpha_{2C}$ receptor antagonist that selectively binds to an $\alpha_{2C}$ adrenergic receptor.

2. The method of claim 1 wherein the antagonist is a reversible $\alpha_{2C}$ adrenergic receptor antagonist.

3. The method of claim 1 wherein the wherein the antagonist is administered prior to exposure of the subject to cold or stress.

4. The method of claim 1 wherein the antagonist is administered after exposure of the subject to cold or stress.

5. The method of claim 1 wherein the antagonist is administered in an oral composition or a topical composition.

6. The method of claim 1 wherein the antagonist is administered in an amount sufficient to increase blood flow through the small arteries or arterioles of the affected organ.

7. The method of claim 1 wherein the patient is exhibiting symptoms of Raynaud's phenomenon.

8. The method of claim 1 wherein the patient is exhibiting symptoms of ischemia of the small arteries or arterioles of an organ selected from the group consisting of kidney, heart, lungs, gastrointestinal tract and combinations thereof.

9. The method of claim 8 wherein the patient has scleroderma.

10. The method of claim 8 wherein the antagonist is administered to the patient in a pharmaceutical composition that is orally ingested or inhaled by the patient or injected into the patient.

11. The method of claim 8 wherein the amount of antagonist administered is from 0.01 μg to about 100 mg of antagonist per kg of body weight.

12. The method of claim 8 wherein the antagonist is administered in multiple doses.

13. A method of reducing cold-induced vasoconstriction of a small cutaneous artery or arteriole in at least one organ or part of a patient's body, comprising contacting the vascular smooth muscle cells of said artery or said arteriole with an $\alpha_{2C}$ receptor antagonist that selectively binds to an $\alpha_{2C}$ adrenergic receptor.

14. A method of reducing constriction of the small arteries or arterioles in an organ selected from the group consisting of heart, lung, kidney, gastrointestinal tract and combinations thereof comprising contacting the vascular smooth muscle cells of said artery or arteriole with an $\alpha_{2C}$ receptor antagonist that selectively binds to an $\alpha_{2C}$ adrenergic receptor.

15. The method of claim 1, wherein the antagonist is a competitive inhibitor of an α2 adrenergic receptor agonist.

16. The method of claim 13, wherein the antagonist is a competitive inhibitor of an α2 adrenergic receptor agonist.

17. The method of claim 14, wherein the antagonist is a competitive inhibitor of an α2 adrenergic receptor agonist.

18. The method of claim 13, wherein the antagonist is a competitive inhibitor of an α2 adrenergic receptor agonist.

* * * * *